(12) United States Patent
Broad

(10) Patent No.: US 12,186,589 B2
(45) Date of Patent: Jan. 7, 2025

(54) LEAF DRIVE MOUNT FOR A MULTI-LEAF COLLIMATOR

(71) Applicant: Elekta Limited, Crawley (GB)

(72) Inventor: Martin Broad, Crawley (GB)

(73) Assignee: Elekta Limited, Crawley (GB)

( * ) Notice: Subject to any disclaimer, the term of this patent is extended or adjusted under 35 U.S.C. 154(b) by 155 days.

(21) Appl. No.: 17/906,149

(22) PCT Filed: Mar. 11, 2021

(86) PCT No.: PCT/EP2021/056278
§ 371 (c)(1),
(2) Date: Sep. 12, 2022

(87) PCT Pub. No.: WO2021/180902
PCT Pub. Date: Sep. 16, 2021

(65) Prior Publication Data
US 2023/0101881 A1 Mar. 30, 2023

(30) Foreign Application Priority Data
Mar. 13, 2020 (GB) ..................... 2003673

(51) Int. Cl.
*A61N 5/10* (2006.01)
*G21K 1/04* (2006.01)
(52) U.S. Cl.
CPC ........... *A61N 5/1045* (2013.01); *G21K 1/046* (2013.01)
(58) Field of Classification Search
CPC ..... A61N 5/1045; A61N 5/1042; G21K 1/046
See application file for complete search history.

(56) References Cited

U.S. PATENT DOCUMENTS

| | | | |
|---|---|---|---|
| 6,459,769 | B1 | 10/2002 | Cosman |
| 7,085,355 | B1 | 8/2006 | Albagli et al. |
| 7,167,542 | B2 | 1/2007 | Juschka et al. |
| 8,384,049 | B1 | 2/2013 | Broad |
| 8,718,234 | B2 | 5/2014 | Echner |
| 2002/0101959 | A1 | 8/2002 | Kato et al. |
| 2006/0193441 | A1 | 8/2006 | Cadman |
| 2009/0262901 | A1 | 10/2009 | Broad et al. |
| 2011/0026683 | A1 | 2/2011 | Broad et al. |
| 2011/0199085 | A1 | 8/2011 | Allen et al. |
| 2012/0076269 | A1 | 3/2012 | Roberts |

(Continued)

FOREIGN PATENT DOCUMENTS

| | | |
|---|---|---|
| CN | 201226257 Y | 4/2009 |
| CN | 202128818 U | 2/2012 |

(Continued)

OTHER PUBLICATIONS

"U.S. Appl. No. 17/906,147 Preliminary Amendment Filed with Application", 8 pgs.

(Continued)

*Primary Examiner* — Kiho Kim
(74) *Attorney, Agent, or Firm* — Schwegman Lundberg & Woessner, P.A.

(57) ABSTRACT

A mount for an array of leaf drive units corresponding to a single leaf bank of a multi-leaf collimator comprises a plurality of separable mounting plates. Each mounting plate comprises an array of mounting holes, and each mounting hole is arranged to receive a respective one of the leaf drive units.

9 Claims, 5 Drawing Sheets

(56) References Cited

U.S. PATENT DOCUMENTS

| | | |
|---|---|---|
| 2017/0087386 A1 | 3/2017 | Mellenberg et al. |
| 2017/0148536 A1 | 5/2017 | Kawrykow et al. |
| 2018/0035969 A1 | 2/2018 | Jin |
| 2018/0161602 A1 | 6/2018 | Kawrykow et al. |
| 2020/0185119 A1 | 6/2020 | Stahl et al. |
| 2021/0290979 A1 | 9/2021 | Liu et al. |
| 2023/0100438 A1 | 3/2023 | Broad |
| 2023/0110626 A1 | 4/2023 | Broad |
| 2023/0113879 A1 | 4/2023 | Broad |
| 2023/0173304 A1 | 6/2023 | Broad |

FOREIGN PATENT DOCUMENTS

| | | | |
|---|---|---|---|
| CN | 204502129 U | | 7/2015 |
| CN | 205460495 U | | 8/2016 |
| CN | 205656865 U | | 10/2016 |
| CN | 205843700 U | | 12/2016 |
| CN | 107929955 A | | 4/2018 |
| CN | 110538387 A | | 12/2019 |
| DE | 3030332 A1 | | 2/1982 |
| EP | 0314214 A2 | | 5/1989 |
| EP | 3053628 A1 | | 8/2016 |
| EP | 3266501 A1 | | 1/2018 |
| GB | 2423909 A | * 9/2006 | ............... A61N 5/10 |
| JP | 2006081585 A | | 3/2006 |
| JP | 2008206563 A | | 9/2008 |
| WO | WO-2008076035 A1 | | 6/2008 |

OTHER PUBLICATIONS

"U.S. Appl. No. 17/906,153 Preliminary Amendment Filed with Application", 8 pgs.

"International Application Serial No. PCT/EP2021/056270, International Search Report dated Jun. 17, 21", (Jun. 17, 2021), 3 pgs.

"International Application Serial No. PCT/EP2021/056270, Written Opinion dated Jun. 17, 2021", (Jun. 17, 2021), 5 pgs.

"International Application Serial No. PCT/EP2021/056276, International Search Report dated Jun. 17, 2021", (Jun. 17, 2021), 3 pgs.

"International Application Serial No. PCT/EP2021/056276, Written Opinion dated Jun. 17, 2021", (Jun. 17, 2021), 5 pgs.

"International Application Serial No. PCT/EP2021/056281, International Search Report dated Jun. 16, 2021", (Jun. 16, 2021), 3 pgs.

"International Application Serial No. PCT/EP2021/056281, Written Opinion dated Jun. 16, 2021", (Jun. 16, 2021), 5 pgs.

"International Application Serial No. PCT/EP2021/056282, International Search Report dated Jun. 16, 2021", (Jun. 16, 2021), 3 pgs.

"International Application Serial No. PCT/EP2021/056282, Written Opinion dated Jun. 16, 2021", (Jun. 16, 2021), 5 pgs.

"United Kingdom Application Serial No. 2003664.6, Examination Report dated Aug. 13, 2020" (Aug. 13, 2020), 7 pgs.

"United Kingdom Application Serial No. 2003679.4, Examination Report dated Sep. 15, 2020", (Sep. 15, 2020), 8 pgs.

"United Kingdom Application Serial No. 2003688.5, Examination Report dated Aug. 14, 2020" (Aug. 14, 2020), 6 pgs.

"United Kingdom Application Serial No. 2003694.3, Combined Search and Examination Report mailed Sep. 15, 2020", 7 pgs.

"International Application Serial No. PCT/EP2021/056278, International Search Report dated Jun. 16, 2021", (Jun. 16, 2021), 3 pgs.

"International Application Serial No. PCT/EP2021/056278, Written Opinion dated Jun. 16, 2021", (Jun. 16, 2021), 6 pgs.

"United Kingdom Application Serial No. 2003673.7, Examination Report dated Sep. 15, 2020", (Sep. 15, 2020), 6 pgs.

U.S. Appl. No. 17/906,147, filed Sep. 12, 2022, Multi-Leafe Collimator Module.

U.S. Appl. No. 17/906,153, filed Sep. 12, 2022, Leaf Actuator for a Multi-Leaf Collimator.

U.S. Appl. No. 17/906,179, filed Sep. 12, 2022, Leaf for a Multi-Leaf Collimator.

U.S. Appl. No. 17/906,181, filed Sep. 12, 2022, Multi-Leaf Collimator.

"U.S. Appl. No. 17/906,181, Non Final Office Action mailed Jul. 5, 2024", 9 pgs.

Translation of JP2008206563A, (2008).

Translation of CN-202128818-U, (2012).

"U.S. Appl. No. 17/906,147, Notice of Allowance mailed Jul. 12, 2024", 8 pgs.

"U.S. Appl. No. 17/906,147, Corrected Notice of Allowability mailed Aug. 1, 2024", 2 pgs.

* cited by examiner

LEAF DRIVE MOUNT FOR A MULTI-LEAF COLLIMATOR

PRIORITY APPLICATIONS

This application is a U.S. National Stage Filing under 35 U.S.C. § 371 from International Application No. PCT/EP2021/056278, filed on Mar. 11, 2021, and published as WO2021/180902 on Sep. 16, 2021, which claims the benefit of priority to United Kingdom Application No. 2003673.7, filed on Mar. 13, 2020; the benefit of priority of each of which is hereby claimed herein, and which applications and publication are hereby incorporated herein by reference in their entireties.

FIELD

The present disclosure relates to a leaf drive mount for a multi-leaf collimator, and a multi-leaf collimator having said mount. The present disclosure also relates to a drive arrangement for a multi-leaf collimator and a multi-leaf collimator having the same.

BACKGROUND

Radiotherapy involves the production of a beam of ionising radiation, usually x-rays or a beam of electrons or other sub-atomic particles. This is directed towards a cancerous region of a patient, and adversely affects the tumour cells causing an alleviation of the patient's symptoms. The beam is delimited so that the radiation dose is maximised in the tumour cells and minimised in healthy cells of the patient, as this improves the efficiency of treatment and reduces the side effects suffered by a patient.

In a radiotherapy apparatus, the beam can be delimited using a beam limiting device such as a 'multi-leaf collimator' (MLC). The multi-leaf collimator includes a large number of elongate thin leaves arranged side to side in an array. The leaves are usually made from a high-atomic-number material, usually tungsten, so that they are substantially opaque to the radiation.

Each leaf is moveable longitudinally so that its tip, or leading edge, can be extended into or withdrawn from the radiation beam. All the leaves can be withdrawn to allow the radiation beam to pass through, or all the leaves can be extended so as to block the radiation beam completely. Alternatively, some leaves can be withdrawn and some extended so as to define any desired shape, within operational limits. The array of leaf tips can thus be positioned so as to define a variable edge to the collimator. A multi-leaf collimator usually consists of two banks of such arrays (i.e. leaf banks), each leaf bank projecting into the radiation beam from opposite sides of the collimator. The variable edges provided by the two leaf banks thus collimate the radiation beam to a chosen cross-sectional shape, usually that of a target tumour volume to be irradiated. That is, the two leaf banks combine to provide an aperture of variable shape for shaping the radiation beam.

The leaves of the leaf banks are driven by an array of leaf drive units. Each leaf drive unit includes a leaf motor arranged to rotate one of the components of the leaf drive unit relative to another. This relative rotational motion translates into linear motion of a corresponding leaf connected at the opposite end of the leaf drive unit to the leaf motor.

It is desirable that the leaf drive units are easily mounted, removed and replaced in the multi leaf collimator to improve repair and maintenance efficiency and reduce radiotherapy device downtime.

SUMMARY

Aspects and features of the present invention are set out in the accompanying claims.

Overview

In a multi leaf collimator, the leaf drive units are fixed to a mount that provides a base from which to push and pull the individual leaves. The mount is usually a plate which is placed behind the trailing (or tail) portion of the leaves, lying in a plane such that the axis of movement of the leaves is normal to that plane.

In known multi-leaf collimators, the mount includes a single mounting plate for receiving all leaf drive units corresponding to an entire leaf bank. If a leaf or leaf nut needs to be accessed (for example if it is damaged/worn and needs to be replaced) the entire mounting plate must be removed along with the entire leaf bank and the corresponding leaf drive units. Once this sub assembly of the multi-leaf collimator is removed, any leaves or leaf drive units can be maintained, repaired or replaced outside of the radiotherapy device. Thus, access to any one of the leaves and/or the various components of the leaf drive units involves removal of a large number of components from the multi-leaf collimator.

To address this problem, the mounting plate is split into sections, each section arranged to receive a subset of the leaf drive units associated with a leaf bank. Thus, only a subset of the leaves of any one leaf bank (and their corresponding leaf drive units) need to be removed and replaced. This provides quicker and easier access to any individual leaves and/or leaf drive units. Furthermore, fewer components of the multi-leaf collimator need to be removed/replaced during maintenance and repair, thus reducing radiotherapy device downtime.

Function of the Mount

In a fully assembled multi-leaf collimator, a plurality of leaf drive units for driving the leaves of one of the two leaf banks are mounted in a single mount, each leaf drive unit being mounted in a mounting hole in a mounting plate of the mount. The mount performs the functions of (i) providing a common reference point for the leaf drive units so that the individual leaves can be positioned reliably relative to each other; and (ii) aligning the leaf drive units with their respective coupling location at the tail of their corresponding leaf so that the angle of coupling between each leaf drive unit and leaf is consistent across the whole leaf bank.

The leaf drive units have at least one part that moves relative to another part thereof. Thus, the leaf drive unit can be said to have a first node (one part of the leaf drive unit) and a second node (another part of the leaf drive unit), wherein the second node is moved relative to the first node by operation of the leaf drive unit. For example, the first node may be a part of a leaf motor casing of the leaf drive unit and the second node may be a part of a leaf nut attached to a leaf, the leaf nut arranged to move linearly relative to the motor casing upon driving (i.e. rotation) of the leaf motor. Alternatively, the first node may be a part of the leaf motor casing and the second node may be a part of a leaf actuator screw attached to the leaf, the leaf actuator screw arranged to move linearly relative to the leaf motor casing upon rotation of the leaf motor.

The leaf drive units are mounted so that relative linear and rotational movement between a first node of each leaf drive unit and the mount is prevented. Thus, the mount serves to provide an anchor for the first node of the leaf drive units so that the leaf drive units engender relative motion between second node the mount, which in turn leads to motion of the individual leaves relative to the mount. The mount itself may be either static or moveable relative to a base of the multi-leaf collimator. Thus, the mount provides an anchor point for reliable relative positioning of the individual leaves, which in turn allows reliable and accurate shaping and positioning of the beam shaping aperture.

Traditional Mounts

In known mounts, the mounting plate (the part of the mount in which the leaf drive units are mounted) is provided as one integrated component. That is, the mounting plate cannot be disassembled to form separate parts having mounting holes for receiving the leaf drive units. Thus, all leaf drive units are coupled to the same individual component of the mount. In other words, known mounts include a single mounting plate for receiving all leaf drive units of one leaf bank of the multi-leaf collimator.

Removal, repair or replacement of any of the leaves or leaf drive unit components can be carried out in situ in the multi-leaf collimator. This can be difficult due to the lack of space available for accessing the various components. If a mount with a single traditional mounting plate is used, the time needed for repair can be relatively lengthy due to the density of the motors. Typically, all of the motor power connectors would have to be disconnected from the control board, which is a risk to reliability. Alternatively, the entire leaf bank, leaf drive unit array and mounting plate can be removed as one along with the mounting plate before the leaf drive unit components (e.g. the leaf actuator screws, or leadscrews) are decoupled from their corresponding leaves. Thus, removal of a large number of other components must be carried out even if only a single leaf drive unit or leaf needs repair, maintenance or replacement.

Mount with Separable Mounting Plates

Embodiments include a mount for an array of leaf drive units corresponding to a single leaf bank of a multi-leaf collimator, the mount comprising: a plurality of separable mounting plates, each mounting plate comprising an array of mounting holes, each mounting hole arranged to receive a respective one of the leaf drive units.

The provision of a mount having separable mounting plates allows removal of a subset of leaf drive units from their installed position in the multi-leaf collimator. That is, a subset of the leaves of one leaf bank together with their corresponding leaf drive units can be removed without disturbing the other leaves and/or leaf drive units of the same leaf bank. Servicing of the individual leaf drive units and/or their corresponding leaves is easier because the fewer the number of leaves and leaf drive units in the removed sub assembly of the multi-leaf collimator, the easier it is to manoeuvre the sub assembly and access the leaf and/or leaf drive unit in need of servicing. Radiotherapy device downtime is reduced as a result.

Coupling Between Adjacent Mounting Plates

In a fully assembled multi-leaf collimator, the separable mounting plates are arranged in the same plane and are removably coupled together. The mounting plates may be coupled together by a releasable coupling member between adjacent mounting plates, or by a common frame, mount or bracket coupled to all mounting plates.

Alternatively, or in addition, the mounting plates may include mutually interlocking parts. That is, each mounting plate and its adjacent mounting plate have interlocking parts. Advantageously, this improves the accuracy, reliability and ease of alignment of the mounting plates.

In embodiments, a first mounting plate is coupled to a second mounting plate adjacent the first mounting plate via the selective interlocking of at least a part of the first mounting plate with at least a part of the second mounting plate. The interlocking is selective in that the second mounting plate can be moved from a position in which the at least a part of the second mounting plate and at least a part of the first mounting plate are interlocked, to a position in which there is no interlocking between the second mounting plate and the first mounting plate. The interlocking limits the movement of the second mounting plate linearly in at least one pair of two opposing directions and or rotationally. Advantageously, the interlocking assists reliable positioning of the mounting plates and therefore the leaf drive units coupled thereto during repair/replacement so that the complexity and cost of repair/replacement is reduced.

Thus, it may be understood that the mounting plate is movable from a first position, in which the second mounting plate is interlocked with the first mounting plate, along an axis to a second position in which the second mounting plate is free from the first mounting plate. In embodiments, the axis may be the first axis described herein (i.e. parallel to the longitudinal direction of the leaves). Advantageously, the second mounting plate can be removed more easily along with the leaf drive units mounted thereto and the corresponding leaves while causing minimal disturbance to the leaf drive units mounted to the first mounting plate and the corresponding leaves attached thereto.

In embodiments, the interlocking parts of the first mounting plate and second mounting plate include a recessed structure on one of the first mounting plate and second mounting plate and a corresponding protruding structure on the other of the first mounting plate and second mounting plate for insertion into the recessed structure. Advantageously, this provides a simple mechanism for preventing movement of the first mounting plate relative to the second mounting plate in one axis (perpendicularly from either side of the protruding or recessed structure) while allowing movement in an axis perpendicular to this (e.g. into/out of the recessed structure).

In embodiments, the recessed structure or protruding structure is elongate, thus allowing movement in an axis perpendicular to these two axes (i.e. parallel to the lengthwise direction of the recessed structure or protruding structure). For example, the recessed structure may be a slot or groove on one of the first mounting plate and second mounting plate, and the protruding structure may be a structure on the other of the first mounting plate and second mounting plate corresponding to the slot or groove for engaging the slot or groove.

Alternatively, or in addition, the protruding structure includes a rib or spine on one of the first mounting plate and second mounting plate, and the recessed structure is a structure on the other of the first mounting plate and second mounting plate for engaging the rib or spine.

In embodiments, the interlocking means prevent movement of the first mounting plate relative to the second mounting plate in the plane of the plates themselves, but allow movement therebetween out of this plane for ease of removal of either mounting plate during servicing. A catch, frame, holder or support may be provided to selectively prevent relative movement between the first mounting plate and second mounting plate along the first axis (i.e. in the direction of travel of the leaves). Thus, all relative movement between the first mounting plate and second mounting plate can be prevented during operation of the multi-leaf collimator. Whereas for servicing, one mounting plate can be slid out from its interlocked position adjacent another mounting plate to a position in which it is free from the adjacent mounting plate and can be replaced simply and accurately back to the same position after servicing.

Advantageously, the interlocking allows simpler removal and replacement of the first and second mounting plates from each other while providing reliable and accurate positioning of the first and second mounting plates relative to each other. It is important that the mounting plates are aligned accurately because this affects how the leaf drive units are aligned with the leaves, which in turn affects the accuracy and reliability of the multi-leaf collimator in use.

Mounting Holes

The mounting holes are provided in a two-dimensional array in each mounting plate. The array provides appropriate alignment between the leaf drive units and the part of the corresponding individual leaves to which they are coupled.

Typically, the leaves are arranged so that the point at which the leaf drive unit is connected thereto is staggered between adjacent leaves. As the leaf drive units can have a maximum width which is greater than the maximum width of each individual leaves, this staggering is necessary to ensure that two adjacent leaf drive units do not interfere with one another. Therefore, the mounting holes in the array are arranged in a staggered fashion such that a column of mounting holes is provided with a pitch in the vertical direction (i.e. the second axis defined herein) of the order of the maximum diameter of the leaf drive units and a pitch in the horizontal direction (i.e. the third axis defined herein) of the order of the maximum thickness of the leaves.

Thus, the two-dimensional array is arranged into a grid comprising rows and columns. The rows extend in a direction across the leaf bank (i.e. substantially parallel to the third axis defined herein) and the columns extend in a direction lying across this direction and perpendicular to the direction of travel of the leaves. The staggering of mounting holes in each column means that a centreline common to the mounting holes of a column is oblique to a centreline common to the mounting holes of a row. Put more simply, the columns are not perpendicular to the rows.

That is, in embodiments, the centre points of mounting holes in the array are aligned in columns extending in a first direction and in rows extending in a second direction lying across the first direction, wherein the first direction is oblique to the second direction.

Advantageously, the leaf drive unit array, when in the configuration described above, reduces or minimises wasted space and the multi-leaf collimator can be more compact as a result. A more compact multi-leaf collimator can be more easily housed and manipulated in a radiotherapy device.

So that the columns of mounting holes across the entire leaf bank can be uniformly spaced, the profile of the mounting plates are configured to allow continuity of the pattern of holes in the array from one mounting plate to the adjacent mounting plate. That is, a cross-section of at least one of the mounting plates in the plane of the mounting plates (i.e. the third plane defined herein) is shaped so that a first edge thereof and a second edge thereof opposite to the first edge are substantially parallel to a centreline common to a column of mounting holes. In this way, the mounting holes of a column adjacent to the first edge or the second edge are uniformly spaced from the edge and a distance from the edge to a centreline common to the mounting holes is uniform.

More generally, the centre points of mounting holes in the array are aligned in columns extending in a first direction, and at least one edge of each of the mounting plates is parallel to the first direction. In embodiments, the centre points of mounting holes in the array are aligned in columns extending in a first direction and in rows extending in a second direction lying across the first direction, wherein the first direction is oblique to the second direction, a first edge each of the mounting plates is parallel to the first direction, and a second edge of each of the mounting plates is parallel to the second direction.

Alternatively, or in addition, the plurality of mounting plates includes a first mounting plate and a second mounting plate arranged adjacent the first mounting plate. The mounting hole centre points in the first mounting plate are arranged in a first series of columns and the mounting hole centre points in the second mounting plate are arranged in a second series of columns. Adjacent columns in the first and second series of columns have a first spacing therebetween. A column in the first series of columns closest to the second mounting plate and the column in the second series of columns closest to the first mounting plate have a second spacing therebetween, the second spacing being equal to the first spacing.

Advantageously, the mounting plates do not disrupt the regular spacing between columns from one plate to the next in the overall array.

In embodiments, the distance between the centreline common to the mounting holes in the column adjacent the first edge of the mounting plate is equal to half the distance between the centrelines of adjacent columns of the mounting plate. If the same is true for the distance between the second edge and the centreline of the column adjacent the second edge, the mounting plates can be interchangeable, because any mounting plate of this design can be used adjacent another mounting plate of the same design while maintaining the regularity of spacing between columns across the whole array.

Typically, six mounting holes are provided per column in the array, but this number can be greater than or less than six depending on how the connection points between the leaves and the leaf drive units are staggered in the leaf bank. In embodiments, the spacing between mounting holes in one column and/or one row of the array is uniform and is sufficient to allow adequate spacing between adjacent leaf drive units to allow them to operate without interfering with one another.

Mounting of the Leaf Drive Units Into the Mounting Plates

The mounting holes in the mounting plates are each arranged to receive a part of a leaf drive unit. Typically, the part received is a part of the leaf motor casing as this performs well as the aforementioned first node of the leaf drive unit. The other components of the leaf drive unit (i.e. the internal parts of the leaf motor, the leaf actuator screw and/or the nut associated therewith) are then free to move relative to the mounting plate.

Each mounting hole is typically a through hole in the mounting plate passing between the faces of the mounting plate. If a through hole is used, a bayonet type fitting between the mounting plate and each leaf drive unit can be adopted. In this type of fitting, the leaf actuator screw is fed through the mounting hole from one side of the mounting plate to the other side until a part of the leaf motor casing engages with the mounting plate. In this configuration, the leaf motors are located on one face of the mounting plate opposite the face closest to the leaves. Thus, the leaf drive units can be removed from the mounting plates by pulling them back through the mounting holes in a direction away from the leaves (i.e. along the first axis in the second direction described herein). Removal of the leaf drive units in this way allows removal and replacement of a leaf drive unit without removal of the entire leaf bank or even without removal of a large subset of the leaf drive units of one leaf bank as is made possible by the use of the separable mounting plates as described above.

Retainer

Once the leaf drive units are inserted into the mounting holes, respective retainers fixed to or integral with the mounting plate fix each leaf drive unit to the mounting plate. In the case of a mount having separable mounting plates, the mount includes a plurality of retainers attached to the mounting plates, each retainer arranged to rigidly couple a respective leaf drive unit to one of the mounting plates.

The main function of the retainer is to prevent linear movement of the first node of the leaf drive unit relative to the mounting plate so that the leaf drive unit cannot be withdrawn from the mounting hole. The retainer may also prevent rotational movement of the first node of the leaf drive unit, although this function can also be achieved by interlocking parts on the leaf drive unit and mounting plate without the use of the retainer.

In traditional mounts, the retainer is a screw mounted in the mounting plate adjacent a respective mounting hole. A head of the screw is arranged to engage with a lip or flange on the leaf drive unit (e.g. on the leaf motor casing) to urge a part of the leaf drive unit onto the face of the mounting plate to hold it in position. The screw must be fully removed so that the screw head is no longer an obstacle which prevents the leaf drive unit from being completely withdrawn from the mounting hole. Once the leaf drive unit is replaced into the mounting hole, the screw can be reinserted into its hole on the mounting plate and tightened to reengage the leaf drive unit.

The problem with this arrangement is that the screw must be completely removed from the mounting plate before the leaf drive unit can be removed or replaced. The screw can easily be dropped and is difficult to remove and replace itself, which increases service time and cost and increases radiotherapy device downtime.

Quick Release Retainer

Embodiments provide a quick-release attachment between the motor and the mounting plate. A retainer (e.g. a screw) in the mounting plate engages a flange (or lip) on the motor casing to couple the motor to the mounting plate. To remove the motor, the screw is slightly loosened, and the motor casing is rotated so that the flange disengages from the screw (a relief in the flange aligns with the screw head) and the motor is decoupled from the mounting plate and can be removed without complete removal of the screw.

In embodiments, the retainer includes a threaded portion arranged to engage with a threaded hole in the mounting plate, and a retaining portion including a retaining face of larger outer diameter than the threaded portion. The axis of the threaded portion lies perpendicular to the plane of the retaining face. The retaining face may be an annular face. If the retainer is a screw or bolt, the retaining portion is the screw head or bolt head itself and the retaining face is the underside of the screw head or bolt head. In use, the retaining face is the part of the retainer that engages the leaf drive unit and urges it against the face of the mounting plate.

More generally, each retainer is positioned adjacent to a respective one of the mounting holes and includes: a head including a retaining face arranged to face the mounting plate, a shaft extending from the head and arranged to rotatably engage with the mounting plate such that rotation of the retainer about the axis of the shaft moves the retaining face closer to or further from the mounting plate.

The part of the leaf drive unit which is engaged by the retainer is preferably the leaf motor casing. The leaf motor casing this provides the ideal 'first node' referred to herein, because it is designed to be static while other parts of the leaf drive unit connected to the leaf motor rotate relative to it. However, any other part of the leaf drive unit which fulfils these criteria can be used to provide the first node.

In embodiments, the leaf motor casing includes an engaging member arranged to provide a surface which engages with the retaining face of the retainer so that the retainer urges the leaf motor casing against the mounting plate. That is, engaging member may be a flange or lip. The engaging member may be the mounting flange described in the detailed description. The engaging member is any part of the leaf motor casing which has a larger diameter or width than the diameter of the mounting hole and a thickness suitable for positioning between the retaining face of the retainer and the face of the mounting plate.

The engaging member has a recess provided therein such that upon rotation of the leaf motor casing relative to the mounting plate, the recess can overlap with the retaining face of the retainer to allow removal of the leaf motor casing from the mounting plate without removal of the retainer from the mounting plate. That is, the leaf motor casing is rotatable between a first position in which the flange is engaged with the retaining face to a second position in which the recess overlaps with the retaining face and the leaf drive unit can be removed entirely from the mounting hole without removing the retainer from the mounting plate.

Advantageously, the retainer does not need to be removed from the mounting plate for removal or replacement of the leaf drive unit.

More generally, each leaf drive unit includes: a motor comprising a casing including an engaging member, wherein at a first rotational position of the casing the engaging member engages the retainer to couple the casing to the mounting plate; and at a second rotational position of the casing the engaging member is disengaged from the retainer.

Embodiments provide a drive arrangement for a multi-leaf collimator comprising: a mounting plate for mounting a leaf drive unit; a retainer attached to the mounting plate; a motor configured to actuate a leaf of the multi-leaf collimator, the motor comprising a casing including an engaging member. At a first rotational position of the casing the engaging member engages the retainer to couple the casing to the mounting plate. At a second rotational position of the casing the engaging member is disengaged from the retainer.

In embodiments, the recess has a curved shape so as to match the shape of the overlapping part of the retainer head. However, it is not essential that the recess has this shape. The recess can have any shape and size so long as it accommodates the overlapping part of the retainer head so as to allow the leaf motor casing to move clear of the retainer head when the leaf motor casing is rotated to the second position.

In embodiments, each mounting hole has two retainers adjacent thereto and spaced apart by 180 degrees around the mounting hole.

In embodiments, retainers positioned between rows or between columns are arranged substantially equidistant between mounting holes such that they can retain two leaf drive units mounted in adjacent mounting holes. That is, each retainer engages the engaging member of more than one motor casing. In some embodiments, a single retainer may retain three, or even four, leaf drive units when positioned substantially equidistant between the corresponding number of mounting holes.

The leaf motor casing has a locating member arranged around the circumference thereof to engage an outer circumferential surface of the retaining head of the retainer. The locating member is arranged such that when the leaf drive unit is fully inserted into the mounting hole and rotated in the direction from the first position toward the second position, the locating member prevents any further rotation of the leaf drive unit in this direction once the leaf drive unit arrives at the second position.

More generally, the casing includes a locating member arranged to engage with the retainer when the motor casing is at the second rotational position so as to prevent further rotation of the motor casing once the motor casing has reached the second position.

Advantageously, this allows ease of locating the second position without clear sight of the leaf motor casing. This aids in the smooth and reliable removal of the leaf drive unit from the mounting hole and thus reduces servicing time.

The locating member may be a protrusion from a part of the leaf motor casing, for example the ridge as described in embodiments in the detailed description herein. In embodiments, the leaf motor casing includes a plurality of locating members corresponding to the number of retainers associated with the mounting hole, each locating member arranged to engage with the retainer head at the second rotational position.

BRIEF DESCRIPTION OF THE DRAWINGS

Specific embodiments are described below by way of example only and with reference to the accompanying drawings in which.

DETAILED DESCRIPTION OF THE DRAWINGS

MLC Assembly
Defining a Useful Co-Ordinates Convention

For ease of description, a cartesian co-ordinates system is defined in the Figures by a mutually perpendicular first axis (y), second axis (z) and third axis (x). The first axis defines a first direction (+y) and a second direction (−y) opposite to the first direction. The second axis defines a third direction (+z) perpendicular to the first direction and a fourth direction (−z) opposite to the third direction. The third axis defines a fifth direction (+x) perpendicular to both the first direction and the third direction and a sixth direction (−x) opposite to the fifth direction. The first and second axes define a first plane (yz), the first and third axes define a second plane (xy) perpendicular to the first plane, and the second and third axes define a third plane (xz) perpendicular to the first and second planes. This co-ordinates system and convention is used consistently throughout the Figures.

Figure 1:
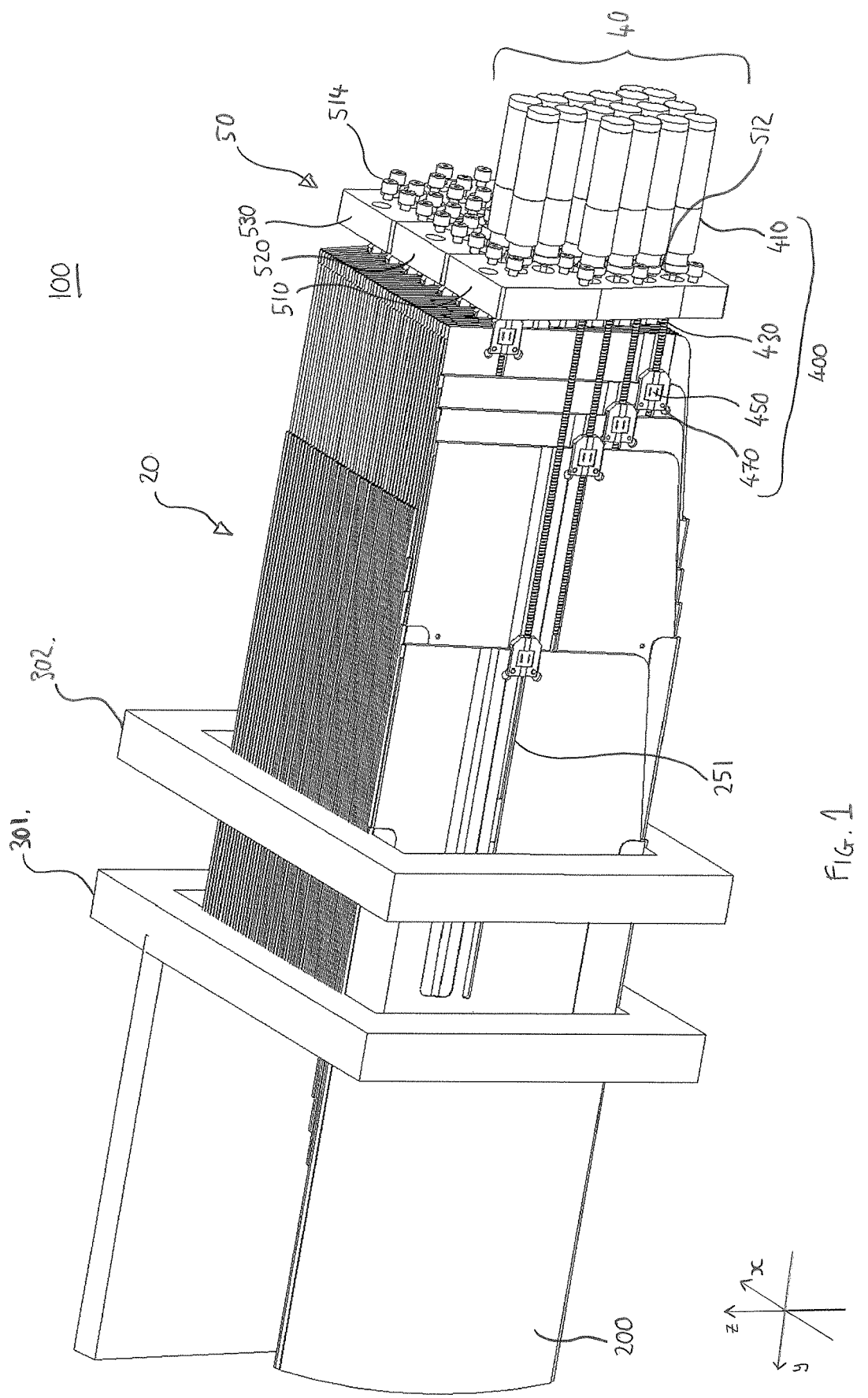
FIG. 1 shows a partially assembled multi-leaf collimator.

FIG. 1 shows a partially assembled multi-leaf collimator 100 comprising a leaf bank 20, a first and second leaf guide 301, 302, a leaf drive array 40 and a leaf drive mount 50.

Figure 6:
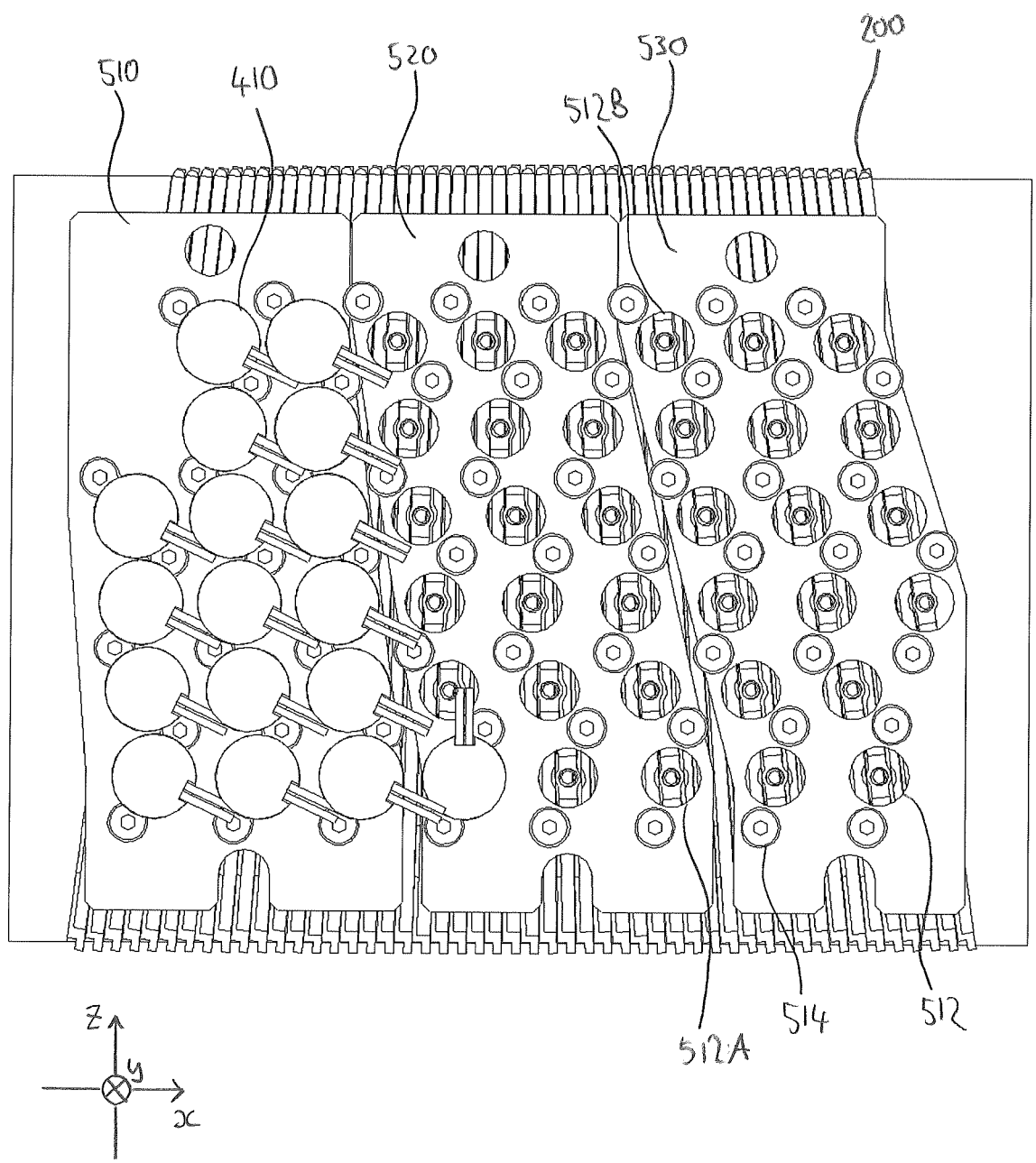
FIG. 6 is an elevation view of the mount.

The leaf bank 20 includes an array of leaves 200 arranged side by side so that a face of one leaf is in contact with a face of an adjacent leaf. The leaves 200 are arranged substantially parallel to each other but a gradient in thickness in the first direction from a first edge of each leaf 200 to a second edge opposite the first edge causes the leaf bank 20 to adopt a trapezoidal cross section in the third plane as shown in FIG. 6. Thus, the plane of a leaf 200 positioned in the middle of the leaf bank 20 is arranged to be substantially parallel to the first plane (yz), but the planes of the other leaves either side of that leaf 200 form a progressively greater angle with the first plane (yz) with distance in the fifth and sixth directions from the centre of the leaf bank 20. The leaves 200 are arranged to move relative to each other in the first and second directions. The leaves 200 are described in more detail below.

The leaf drive array 40 includes a plurality of leaf drive units 400. Each leaf drive unit 400 includes a leaf motor 410, a leaf actuator screw 430, a leaf nut 450 and a leaf nut holder 470. The leaf actuator screw 430 is coupled to the leaf motor 410 and is arranged so that its axis is parallel to the first direction. The leaf motor 410 is arranged to rotate the leaf actuator screw 430 about its axis (i.e. clockwise and anti-clockwise around the first direction). The leaf nut 450 is held in position in a leaf actuator screw slot 250 in the leaf 200 by a leaf nut holder 470 fixed to the leaf 200. The leaf nut 450 is held by the leaf nut holder 470 to be static relative to the leaf 200, with the exception that a small amount of relative linear motion between the leaf nut 450 and the leaf 200 is allowed in the third and fourth directions. The leaf nut 450 contains features which interact with the leaf 200 to keep the leaf nut 450 rotationally static relative to the leaf 200. The leaf nut 450 is arranged to receive the leaf actuator screw 430 and to guide it into the leaf actuator screw slot 250. The rotational motion of the leaf actuator screw 430 translates into linear motion of the leaf nut 450, and hence the leaf 200, relative to the leaf actuator screw 430.

The leaf drive units 400 are staggered in the first direction so that the leaf nut holder 470 of any one leaf does not interfere with the leaf nut holders 470 of the leaves 200 immediately adjacent to it on either side. The leaves 200 also contain grooves to accommodate the portions of the leaf nut holders 470 of adjacent leaves 200 which are proud from the face of the leaf 200. The leaf motor 410, leaf nut 450, leaf nut holder 470 and the grooves in the leaves are described in more detail below.

The leaf drive mount 50 includes three separate mounting plates 510, 520, 530 arranged in a plane parallel to the third plane (xz). The leaf drive mount includes mounting holes 512 therein for receiving the leaf motors 410 and mounting screws 514 for securing the leaf motors 410 to the mounting plates 510, 520, 530. The leaf drive mount 50 and each of its components are described in more detail below.

The first and second leaf guide 301, 302 each comprise a rectangular frame for guiding and supporting the leaves 200 in their linear motion in the first and second directions respectively into and out of the path of the radiation beam.

A complete multi-leaf collimator assembly further includes a second, opposing arrangement including leaf bank, leaf guides, leaf drive array and leaf drive mount which are arranged to substantially mirror the assembly described above relative to a plane parallel to the third plane (xz) and aligned with the centre of the axis of the radiation beam.

In use, the leaf drive arrays drive the leaves 200 of their respective leaf banks 200 to move into and out of the path of a radiation beam passing in the fourth direction through an aperture formed between the leading edges of the leaves 200 of one leaf bank 20 and those of the leaves 200 of the opposing leaf bank 20. The leaves 200 of each leaf bank 20 are moveable independently of each other, which enables the shape of the aperture to be changed according to treatment requirements. The aperture acts as a beam shaper by blocking portions the radiation beam to redefine its cross-sectional shape in the second plane (yz). That is, the radiation beam having passed through the aperture takes on the cross-sectional shape of the aperture in the second plane (yz).

Leaf Actuator Screw

Figure 2:
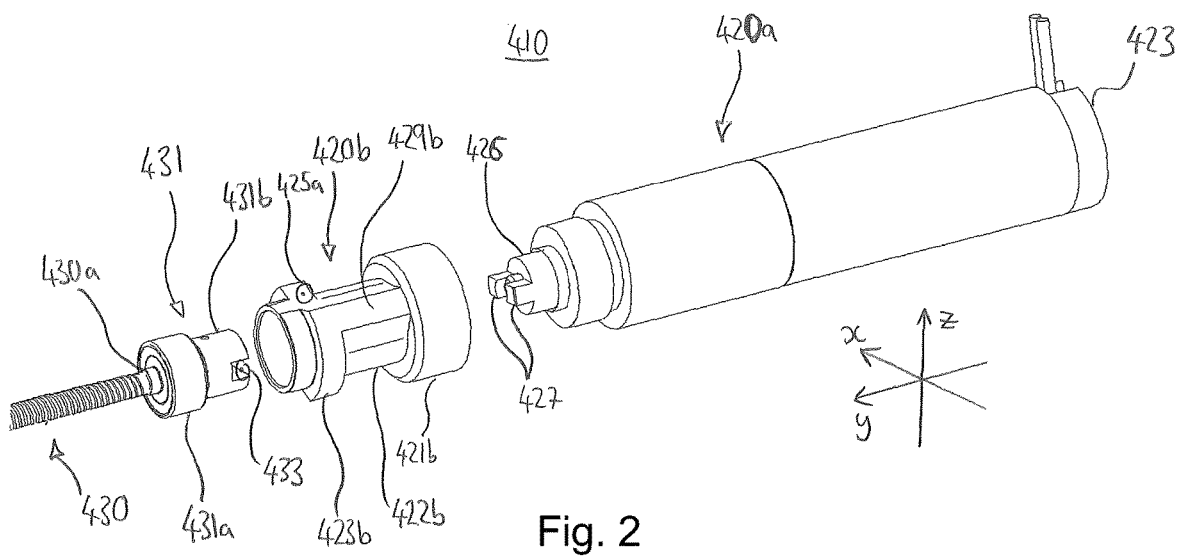
FIG. 2 shows an exploded view of one implementation of a leaf motor and the interface between the leaf actuator screw and the leaf motor.

FIG. 2 shows an exploded view of one implementation of a leaf motor 410 and the interface between the leaf actuator screw 430 and the leaf motor 410. The leaf actuator screw 430 includes a first coupling member 431 fixed to the end of the non-threaded section 430a. The first coupling member 431 comprises a first cylindrical section 431a for receiving and forming a rigid connection with the non-threaded section 430a of the leaf actuator screw 430. A second cylindrical section 431b having a smaller diameter than the first cylindrical section 431a extends in the second direction from an end face of the first cylindrical section 431a. The second cylindrical section 431b has a coupling groove 433 formed across an end face thereof.

Leaf Motor

In the implementation shown in FIG. 2, the leaf motor 410 includes a leaf motor casing 420. The leaf motor casing includes a first casing 420a and a second casing 420b removable from the first casing 420a. The leaf motor 410 further includes a second coupling member 426 fixed to an output shaft of the motor and having coupling protrusions 427 arranged to interlock with the coupling groove 433 in the second cylindrical section 431b of the first coupling member 431.

The first casing 420a is arranged to enclose a rotor, stator and commutator of the leaf motor 410, but not the second coupling member 426, which protrudes from an end of the first casing 420a. The first casing 420a includes a main section including two cylindrical tubes having the same diameter and arranged end to end. At a first end of the main section, the casing has a neck smaller in diameter than the main section. The neck includes a flange which forms a terminal end of the first casing 420a, the second coupling member 426 protruding in the first direction from said terminal end.

At a second end of the main section opposite the first end, there is an end cap 423 having the same diameter as the two cylindrical tubes. The end cap 423 has a wiring cutaway in one part of the circumferential region of the end cap 423 for allowing two wires connected to the internal components of the leaf motor 410 to protrude side by side from the end cap 423 in a radial direction of the end cap 423.

The second casing 420b includes a cap section 421b arranged to fit over the neck and flange of the first casing 420a. The second casing also includes a neck section 422b having a diameter smaller than that of the cap section 421b, the neck section having the leaf motor casing mounting flange 425 described earlier around the circumference thereof. The second casing 420b is arranged to house the first coupling member 431 and second coupling member 426 in the neck section 422b thereof.

Motor with Integral Casing and Integral Leadscrew

Figure 3:
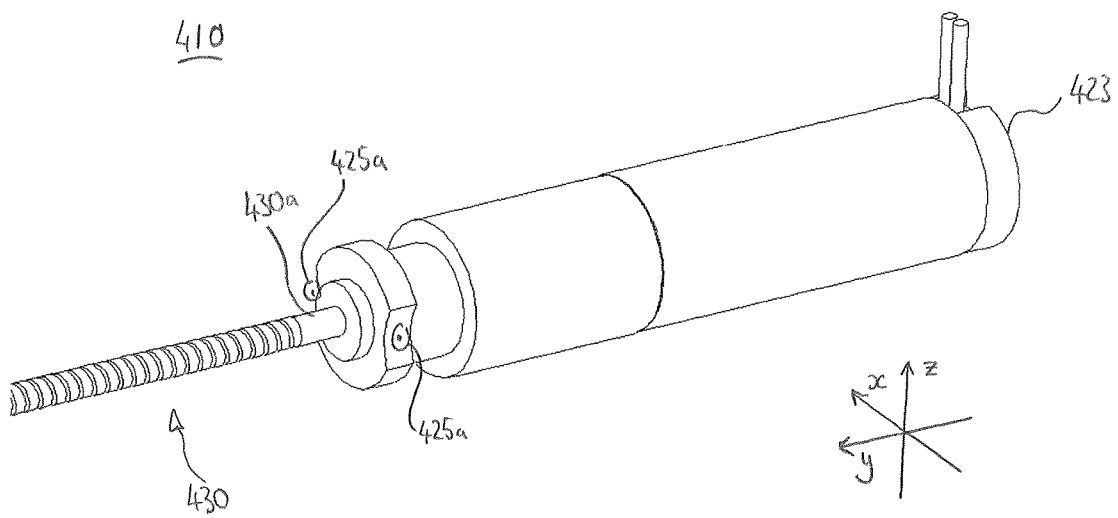
FIG. 3 shows a different implementation of the leaf motor to that shown in FIG. 2.

FIG. 3 shows a different implementation of the leaf motor 410 than that shown in FIG. 2. In the implementation of FIG. 3, the leaf motor 410 includes a leaf motor casing 420 having substantially the same outer appearance as the first casing 420a and second casing 420b described above. In this implementation, the leaf motor casing 420 is also arranged to enclose the rotor, stator and commutator. However, instead of being removably coupled to the motor output shaft, the leaf actuator screw 430 is integrally formed with the motor output shaft. Put another way, the leaf actuator screw 430 is the motor output shaft. That is, the motor output shaft and the leaf actuator screw may be formed from one monolithic rod.

The leaf motor casing 420 includes a main section including two cylindrical tubes having the same diameter and arranged end to end. At a first end of the main section, the casing includes a neck smaller in diameter than the main section and connected by a shoulder to the main section. The neck includes a mounting flange 425, which is substantially the same as that described with reference to FIG. 2. At a second end of the main section opposite the first end, there is an end cap 423 substantially the same as the end cap described with reference to FIG. 2.

The neck of the leaf motor casing 420, the mounting flange, the shoulder connecting the neck to the main section and the cylindrical tube adjacent the shoulder are monolithic. Alternatively, these parts of the leaf motor casing are separate but pressed/bonded together so that they are not removable without deformation. That is, these parts of the leaf motor casing are integrally formed so that they are not removable from each other.

Mounting of the Leaf Motor in the Mounting Plate

Figure 4A:
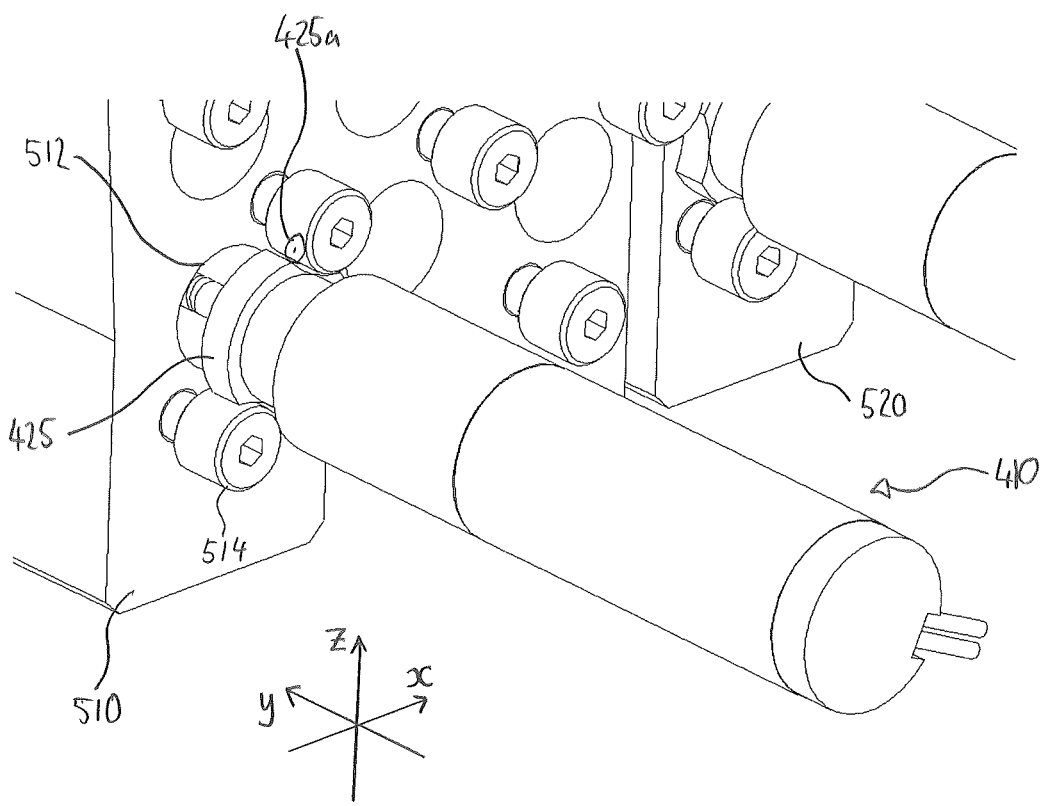
FIGS. 4a and 4b each show an isometric view of leaf motor of FIG. 3 and the mounting thereof in one of the mounting plates.
Figure 4B:
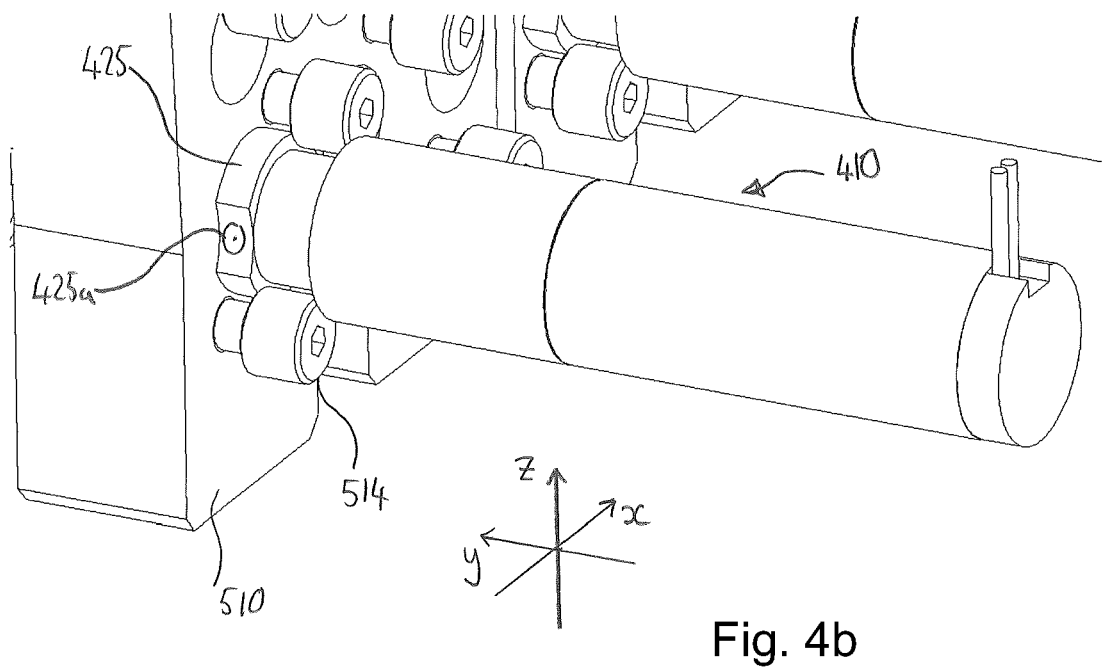

FIGS. 4a and 4b each show an isometric view of leaf motor 410 of FIG. 3 and the mounting thereof in one of the mounting plates 510. FIG. 4a shows the rotational position of the leaf motor relative to the mounting plate upon insertion or removal of the leaf motor from the mounting hole 512. FIG. 4b shows the rotational position of the leaf motor 410 relative to the mounting plate when the leaf motor is inserted into the mounting hole 512 and locked in position by two mounting screws 514.

As described earlier, the leaf motor casing 420 is mounted to a respective mounting plate 510 by two mounting screws 514 cooperating with the mounting flange 425 to hold the mounting flange 425 to the second face of the mounting plate 510. The mounting flange 425 further includes two curved recesses 425a each arranged to receive an edge of the head of a corresponding mounting screw 514 located to one side of the mounting hole 512 in the mounting plate 510. The two curved recesses 425a are at opposite positions relative the central axis of the leaf motor casing 420, so that in a particular rotation of the leaf motor 410 about the first direction, they are able to locate with corresponding mounting screws 514 positioned on opposite sides of the mounting holes 512. The curved recess 425a has a shape and dimensions which correspond to those of the part of the head of the mounting screw 514 which normally overlaps the mounting flange 425.

Thus, by turning the leaf motor casing 420 about its axis, it can adopt one of two rotational positions relative to the respective mounting plate 510. The two rotational positions include a first rotational position (see FIG. 4a) in which the mounting screws 514 each completely overlap a respective curved recess 425a in the mounting flange 425, and a second rotational position (see FIG. 4b) in which the mounting screws 514 each overlap a portion of the mounting flange 425.

In the first rotational position, the end of the leaf motor 410 can be inserted into the mounting hole 512 in the mounting plate 510 even when the corresponding mounting screws 514 are in position in the mounting plate 510. This is because each curved recess is arranged to receive the edge of the head of the mounting screw 514. Following insertion of the end of the leaf motor 410 into the mounting hole 512, the leaf motor casing 420 can be rotated to the second rotational position.

In the second rotational position, the leaf motor casing 420 can be held against the mounting plate 510 by tightening the mounting screws 514 so as to urge the mounting flange 425 against the second face of the mounting plate 510.

By loosening the mounting screws 514, the leaf motor casing 420 can be rotated back to the first rotational position. In the first rotational position, the leaf motor casing 420 can also be removed from the mounting hole 512 in the mounting plate 510 even when the corresponding mounting screws 514 are in position in the mounting plate 510, again because the two curved recesses 425a are each shaped and dimensioned to receive the edge of the head of a respective mounting screw.

Referring back to FIG. 2, a ridge 429b may be located in neck section 422b between the cap section 421b and the mounting flange 425. The top surface of the ridge 429b (i.e. the surface distal from the outer circumferential surface of the neck section 422b) is flush with the outer circumferential surface of the mounting flange 425. The sides of the ridge cross section are convex and the circumferential position of the ridge 429b around the neck section 422b is such that one side of the ridge 429b is flush with one half of the curved recess 425a. The shape and position of the ridge 429b are such that the side surface of the ridge flush with the curved recess 425a acts as a locating surface for the curved recess 425a. The purpose of the ridge 429b is to increase the cross section of the neck section 422b because the wall thickness of the neck section 422b is typically fairly thin. Thus, the ridge 429b gives the neck section 422b greater stiffness. Additionally, the ridge 429b acts as a stop (i.e. locating means) and limits the rotation of the leaf motor casing 420 once it is engaged under the head of the mounting screw 514. Visibility of the mounting screws 514 is limited due to motors and components obscuring the view. The ridge 429b assists in collocating the curved recess 425a and the mounting screws 514. If the ridge 429b was not present it would be possible to continue rotating the leaf motor casing 420 until the mounting flange would be inadvertently engaged/ disengaged with the screw heads again.

That is, without the ridge 429b, sight of the mounting flange 425 is necessary to ensure that the leaf motor casing 420 can be rotated accurately to the first rotational position when the leaf motor 410 is inserted into the mounting hole 512. Otherwise the leaf motor 410 must be pulled in the second direction while rotating. However, with the ridge 429b included, the leaf motor casing 420 can be rotated until the head of the mounting screw meets the locating surface of the ridge 429b. The first rotational position is then assured and the leaf motor 410 can be removed from the mounting hole 512. A corresponding ridge is located on the opposite side of the neck section 422b to provide a locating surface for the corresponding curved recess 425a on the opposite side of the flange.

Leaf Drive Mount

Figure 5:
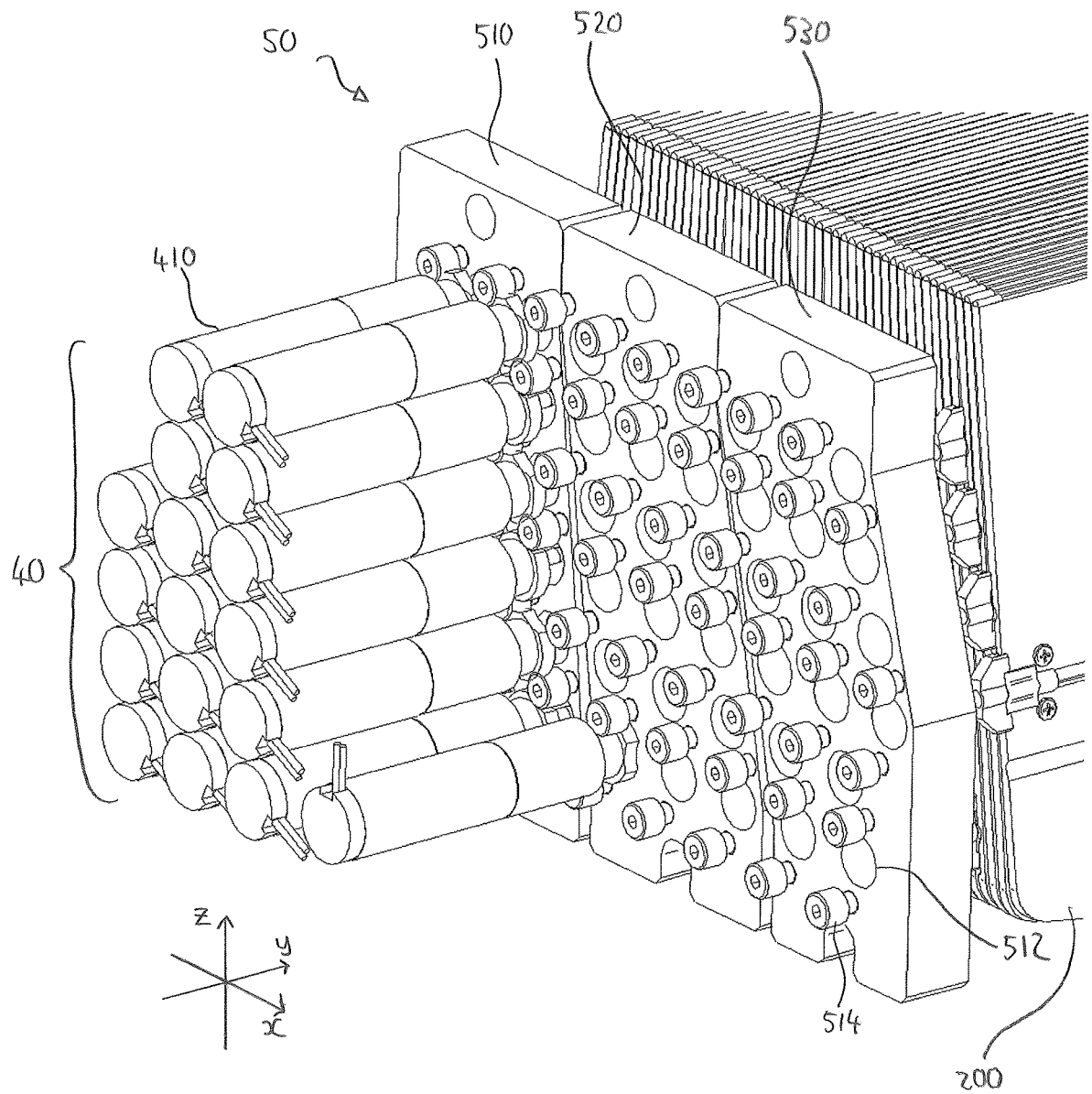
FIG. 5 is an isometric view of a mount.

FIGS. 5 and 6 show detailed views of the leaf drive mount 50 in situ with the other components of the multi-leaf collimator assembly 100. FIG. 5 is an isometric view and FIG. 6 is an elevation view in the first direction.

As shown in FIGS. 5 and 6, the leaf drive mount includes a first mounting plate 510, a second mounting plate 520 and a third mounting plate 530. The mounting plates 510, 520, 520 are separable from each other to facilitate ease of servicing and maintenance.

Each of the mounting plates 510, 520, 530 has a first face parallel to the third plane (xz) and proximal to the leaves 200, and a second face parallel to the first face and distal from the leaves 200. In use, the leaves 200 are situated between the leaf drive mount 50 and the path of the radiation beam, such that the leaf drive mount 50 lies behind a tail portion 220 of the leaves 200 and intersects the plane of each of the leaves 200.

Each of the mounting plates 510, 520, 530 contains a two-dimensional array of mounting holes 512, each of the mounting holes 512 having a central axis in the first direction and passing through the mounting plate 510 between the first face and the second face. Each of the mounting holes 512 is arranged to receive the cylindrical neck of a leaf motor casing 420 of one of the leaf motors 410 inserted into the mounting hole 512 in the first direction from the side of the mounting plate 510 having the second face. The leaf actuator screw 430 corresponding to the respective leaf motor 410 passes through the mounting hole 512 and emerges from the side of the mounting plate 510 having the first face. The mounting flange 425 of the leaf motor casing 420 is arranged to engage with the second face of the mounting plate 510 so as to prevent the whole of the neck of the casing from being insertable into the mounting hole 512. Thus, the leaf motor movement in the first direction is restricted by the mounting flange 425.

Each of the mounting plates 510, 520, 530 includes an array of threaded holes in the second face thereof for receiving respective mounting screws 514. When in situ in the threaded holes, the mounting screws 514 are arranged to overlap a face of the mounting flange 425 distal from the mounting plate 510 so as to prevent movement of the leaf motor 410 in the second direction.

The 2D array of mounting holes 512 in each mounting plate 510, 520, 530 includes three columns. Each of the columns is arranged at an acute angle to the third direction to take into account the staggered positioning of the leaf drive units 400 described earlier. The array is arranged in six rows, and the pattern of staggering of the leaf drive units 400 repeats every six leaves in the fifth direction.

As shown in FIG. 6, the sides of the mounting plates are angled to be substantially parallel to the angled columns. This allows consistent spacing of the leaf drive units 400 in the fifth direction by permitting a separation of the order of the width of a leaf 200 between a first mounting hole 512A in the final row of the final column of one mounting plate 520 and a second mounting hole 512B in the first row of the first column of an adjacent mounting plate 530.

A mounting screw 514 (i.e. the aforementioned retainer) is arranged on two opposing sides of every mounting hole 512. The mounting screws form a 2D array having rows between the rows of mounting holes 512 and columns between the columns of mounting holes. The mounting screws are positioned such that one mounting screw 514 can interact with one leaf motor in the mounting hole row above and one leaf motor in the mounting hole row below. Thus, the number of mounting screws can be reduced.

It may be understood that when the terms 'parallel', 'perpendicular' or 'in the plane of' are used to describe the relative arrangement of features and components, small deviations therefrom are permitted provided that they do not affect the functional and/or operational aspects of the multi-leaf collimator modules described herein.

Features of the above aspects can be combined in any suitable manner. It will be understood that the above description is of specific embodiments by way of aspect only and that many modifications and alterations will be within the skilled person's reach and are intended to be covered by the scope of the appendant claims.

The invention claimed is:

1. A multi-leaf collimator comprising:
    a leaf bank including an array of individually moveable leaves;
    an array of leaf drive units corresponding to the leaf bank, the leaf drive units each configured to drive the linear movement of a respective leaf; and
    a mount for the array of leaf drive units, the mount comprising:
        a plurality of separable mounting plates, each mounting plate comprising an array of mounting holes, each mounting hole arranged to receive a respective one of the leaf drive units; and
        a plurality of retainers attached to the plurality of separable mounting plates, each retainer arranged to rigidly couple a particular leaf drive unit to a particular mounting plate of the plurality of separable mounting plates, wherein each leaf drive unit is received in a respective mounting hole and includes a motor comprising a casing including an engaging member, wherein at a first rotational position of the casing the engaging member engages the retainer to couple the casing to the particular mounting plate, and wherein at a second rotational position of the casing the engaging member is disengaged from the retainer.

2. The multi-leaf collimator according to claim 1, wherein center points of the mounting holes in the array are aligned in columns extending in a first direction and in rows extending in a second direction oblique to the first direction.

3. The multi-leaf collimator according to claim 1, wherein center points of the mounting holes in the array are aligned in columns extending in a first direction, and at least one edge of each of the mounting plates is parallel to the first direction.

4. The multi-leaf collimator according to claim 1, wherein center points of the mounting holes in the array are aligned in columns extending in a first direction and in rows extending in a second direction oblique to the first direction, wherein a first edge each of the mounting plates is parallel to the first direction, and wherein a second edge of each of the mounting plates is parallel to the second direction.

5. The multi-leaf collimator according to claim 1, wherein the plurality of separable mounting plates includes a first mounting plate and a second mounting plate arranged adjacent to the first mounting plate, wherein center points of each mounting hole in the first mounting plate are arranged in a first series of columns and center points of each mounting hole in the second mounting plate are arranged in a second series of columns, wherein adjacent columns in the first series of columns and the second series of columns have a first spacing therebetween, and wherein a particular column in the first series of columns closest to the second mounting plate and a particular column in the second series of columns closest to the first mounting plate have a second spacing therebetween, the second spacing being equal to the first spacing.

6. The multi-leaf collimator according to claim 1, wherein each retainer is positioned adjacent to a mounting hole and includes:
    a head including a retaining face arranged to face the mounting plate; and
    a shaft extending from the head and arranged to rotatably engage with the mounting plate such that rotation of the retainer about an axis of the shaft moves the retaining face closer to or further from the mounting plate.

7. The multi-leaf collimator according to claim 1, wherein the engaging member is a flange having a recess.

8. The multi-leaf collimator according to claim 1, wherein the casing includes a locating member arranged to engage with the retainer when the motor casing is at the second rotational position so as to prevent further rotation of the motor casing once the motor casing has reached the second rotational position.

9. The multi-leaf collimator according to claim 1, wherein the retainer engages the engaging member of more than one motor casing.

* * * * *